United States Patent [19]

McNeal

[11] Patent Number: 4,707,863
[45] Date of Patent: Nov. 24, 1987

[54] ANTI-FOG GOGGLE WITH FOAM FRAME

[75] Inventor: Joseph R. McNeal, Ketchum, Id.

[73] Assignee: Scott USA Limited Partnership, Ketchum, Id.

[21] Appl. No.: 832,103

[22] Filed: Feb. 19, 1986

Related U.S. Application Data

[63] Continuation-in-part of Ser. No. 460,510, Jan. 24, 1983, Pat. No. 4,571,748.

[51] Int. Cl.$^4$ ............................................. A61F 9/02
[52] U.S. Cl. ......................................... 2/436; 2/439
[58] Field of Search .................. 2/436, 437, 439, 431, 2/432, 426, 435, 447, 452

[56] References Cited

U.S. PATENT DOCUMENTS

| | | | |
|---|---|---|---|
| 540,746 | 6/1895 | Lamb | 2/439 |
| 2,388,205 | 10/1945 | Bernheim et al. | 2/437 X |
| 4,447,914 | 5/1984 | Jannard | 2/436 X |
| 4,571,748 | 2/1986 | Carroll et al. | 2/436 |

FOREIGN PATENT DOCUMENTS 0150848  9/1981  German Democratic Rep. .... 2/436

Primary Examiner—Peter Nerbun
Attorney, Agent, or Firm—Jenner & Block

[57] ABSTRACT

An anti-fog goggle is provided having a foam frame with a method of manufacturing the goggle. The goggle is composed of generally planar individual members, yet the goggle has a desired degree of self-supporting curvature. The anti-fog goggle has a semi-rigid support member for supporting the goggle's lens, the support member being stamped out of a planar sheet of foam. The foam support member has air channels depressed therein through which air enters and exits the interior of the goggle to prevent condensation from forming on the viewing surface of the lens' interior. The lens is stamped from a planar sheet of transparent plastic which is deformable into a simple curve. The lens is formed with a plurality of apertures therein which are aligned with air channels in the support member when the lends is secured thereto. The lens' apertures form ports through which air may flow into the air channels, the air channels directing the air downward across the inner surface of the lens. To make the goggle, the support member is curved about a form having the generally desired curvature and the lens adhered to the curved support member with an adhesive to deform the lens and support member into the form curvature which is substantially maintained when the lens and support member are removed from the form. The goggle may also include a cushioning foam member which is adhered to the inner surface of the semi-rigid foam support member to cushion contact with the wearer's face.

40 Claims, 7 Drawing Figures

ANTI-FOG GOGGLE WITH FOAM FRAME

This is a continuation-in-part of U.S. patent application Ser. No. 460,510 filed Jan. 24, 1983 now patent no. 4,571,748.

TECHNICAL FIELD

The present invention relates to an anti-fog goggle and the method of manufacturing the goggle. More specifically, the present invention relates to an anti-fog goggle having a foam support member for supporting the goggle's lens, the support member having air channels therein through which air enters and exits the interior of the goggle to prevent condensation from forming on the viewing surface of the lens' interior.

BACKGROUND OF THE INVENTION

Many recreational activities and sports, such as skiing and motorcycle riding or racing, require participants to wear goggles. Known goggles typically include a frame of rubberized plastic having sufficient rigidity to grip a lens and yet with sufficient pliability so as to deform under forces applied by a goggle strap positioned about the head of the goggle wearer so that the frame more closely conforms to the shape of the wearer's face. In order to maintain a spaced relation between the lens and the face of the goggle wearer, and to further allow air to enter into and exit from the interior of the goggle to prevent the inner surface of the lens from fogging, frames of rubberized plastic are generally curved and intricately shaped. These frames are typically manufactured by injection molding which requires expensive tooling due to the curvature and intricate frame configuration. In order to enable the manufacturer to recapture his tooling costs, these goggles are relatively expensive.

SUMMARY OF THE INVENTION

In accordance with the present invention, the disadvantages of prior goggles, as discussed above, have been overcome. All of the goggle components can be made as generally planar members and easily assembled in a manner that provides the desired self-sustaining goggle curvature.

In accordance with one embodiment of the present invention, the goggle includes a foam or cellular plastic support member for supporting the goggle lens. The support member has at least one and preferably a plurality of air channels formed therein to allow air to enter into and exit from the interior of the goggle to reduce or prevent condensation from forming on the viewing surface of the lens interior. Because of its unique construction, the goggle of the present invention is extremely lightweight, more comfortable to wear than prior goggles, and inexpensively manufactured.

More specifically, the goggle of the present invention includes a transparent, normally planar lens that is deformed into a curve, the lens having a centrally located viewing area and non-viewing areas adjacent the upper and lower edges of the viewing area. In accordance with one lens embodiment, in the upper non-viewing area of the lens, at least one and preferably a plurality of apertures may be present to provide ports through which air may enter.

The lens supporting member is formed from a generally planar sheet of foam material of, or that can be compressed to, sufficient density, to provide a semi-rigid member. The support member, in the assembled goggle, is deformed into a curve conforming with the lens curvature. The normally planar lens and frame are secured together in the desired curvature. The combination of the lens and support member secured together provides a goggle with curvature that is self-sustaining. Usually, the support member and lens member will be adhesively secured together to form an adhesive bond while the members are placed in a curved position. While other forms of securing could be used, such as mechanical fasteners, adhesively securing the goggle members is preferred.

The support member can be obtained in any suitable manner. For example, it is contemplated that the support member can be stamped or cut from the sheet foam material to provide the desired planar configuration. Thereafter, the desired contours and air channels can be formed.

The support member has a centrally located opening defining the viewing area of the lens. The support member has upper and lower areas which are respectively contiguous with and define the upper and lower non-viewing areas of the lens.

The air channels of the support member are formed in the upper and lower areas of the outer surface of the support member with the upper air channels being aligned with the lens apertures to allow air to enter the upper air channels through the apertures. The air channels and desired contours can be formed by heat pressing the support member at the locations where the air channels or contours are desired, for example, or by otherwise forming the air channels by any suitable method, such as by cutting the frame member. Air entering the apertures passes through the upper air channels between the lens and support member so as to be directed downward into the interior of the goggle and out through the lower air channels. Air passing across the inner surface of the lens prevents the lens from fogging.

The goggle also preferably includes a layer of a generally planar, soft, flexible, cushioning material which is mounted to the inner surface of the support member. While the support member itself may provide cushioning, it is often desirable to provide additional cushioning. The cushioning material may be stamped out or cut from a planar sheet of suitable foam material which can be of the same type as used for the support member but which is less dense so as to cushion contact with and conform to the face of the goggle wearer.

The individual goggle components (the support member, lens and cushioning material) prior to assembly are normally planar. That is, the components are planar absent a deformation force.

The goggle is assembled from the individual normally planar components with ease on a curved form defining the general shape of the goggle curvature that is desired. The form may provide a simple curve, such as a generally circular arc, or a relatively complex curve, as desired. The form has a radius (or radii) of curvature which is slightly less than the desired radius (or radii) of curvature of the finished goggle. Thus, the form defines a curved assembly position that is of somewhat greater curvature than the desired final goggle curvature or assembled curvature. In one embodiment, the desired goggle curvature is a generally circular arc and the form is thus generally circular. The planar cushioning member, if present, is first secured about the form with a strap or the like so that the member conforms to the shape of the form. Adhesive is next applied to the outer surface of the cushioning member to secure by adhesive bonding the cushion to the support member positioned on top thereof in a manner to conform with the shape of the form. While the support member is curved about the form, the planar lens is positioned in alignment over the support member and secured to the support member, such as with a suitable adhesive. As the lens is adhered to the support member, curved about the form, the planar lens is deformed into the curved assembly position.

After the adhesives are cured or set to provide an adhesive bond between the support member and lens, the curve of the lens and the support member, and thus the goggle, is generally maintained but relaxed somewhat when the bonded goggle components are removed from the form, such that the radius of curvature of the lens and goggle is slightly greater than the radius of the form providing the final or assembled curvature. The final degree and type of goggle curvature can be adjusted by merely controlling the degree and type of assembly curvature and making appropriate allowances for the curvature relaxation that occurs when the goggle is released from the form. Thus, a goggle having a self-sustaining curvature is provided that can be constructed entirely of members that, by themselves, are normally planar.

BEST MODE FOR CARRYING OUT THE INVENTION

Figure 1:
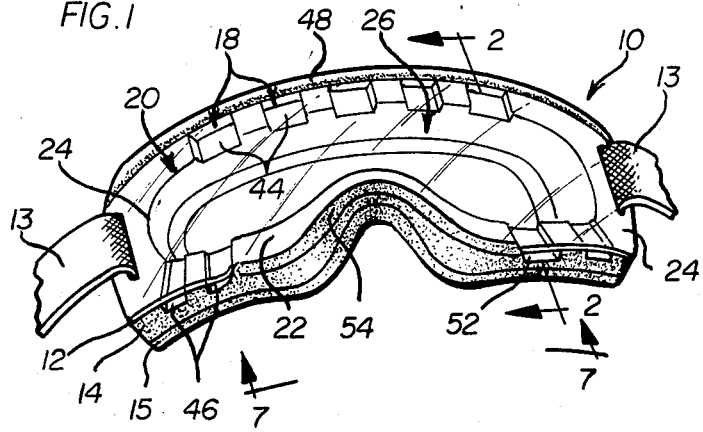
FIG. 1 is a perspective view of the anti-fog goggle of the present invention.
Figure 2:
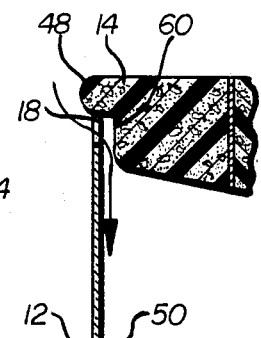
FIG. 2 is a cross-sectional view of the goggle taken approximately along the line 2—2 of FIG. 1.
Figure 3:
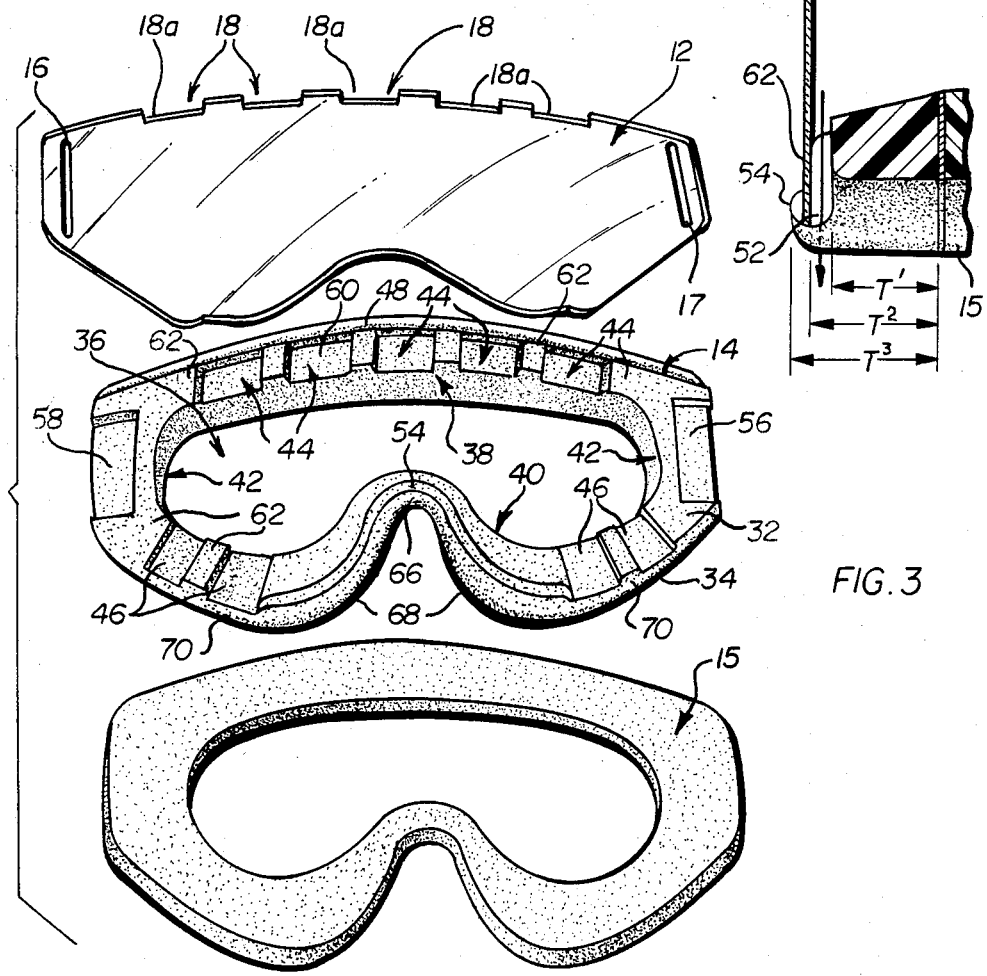
FIG. 3 is a perspective view of the planar components of the goggle, i.e., the lens, foam frame and cushioning member, before assembly.

As shown in FIGS. 1, 2 and 3, the goggle 10 of the present invention includes a lens 12, a foam support member 14 secured to the inner surface thereof and a foam cushion 15 which is secured to the inner surface of the support member 14 to cushion contact with the face of the goggle wearer. The goggle 10 also includes a strap or headband 13, that is preferably adjustable, to secure the goggle about the wearer's head, only a portion of the strap being shown.

The lens 12, which by itself is planar, is stamped or cut out of a planar sheet of semi-rigid, transparent plastic which may be deformed into a curve. Generally, the sheet of plastic is of uniform thickness. Suitable plastic lens materials are known in the art and include, for example, cellulose propionate materials and polycarbonate materials. Cellulose propionate, also known as cellulose acetate propionate, is a preferred material and can readily be treated with an anti-fog polymer as known in the art. Preferably, the side of the lens that faces the wearer is treated with an anti-fog material.

The lens 12 has an elongated shape with a pair of strap slots 16 and 17 formed in opposite ends thereof during the stamping process. Also formed during the stamping process are a number of spaced apertures 18 located in an upper, non-viewing area 20 of the lens, the apertures forming ports through which air may enter into the interior of the goggle 10 as discussed below. The upper, lower and side non-viewing areas 20, 22 and 24 of the lens 12, as well as a centrally located viewing area 26 of the lens, are defined by the lens support member 14 which is contiguous with the lens about its periphery.

The support member 14, which by itself is planar, is stamped or cut out of a planar sheet of cellular plastic (plastic foam) having a uniform thickness and can be heat pressed, also known as felting, to form the desired contours on the outer surface 32 and inner surface 34 of the member so that the member 14 is formed having cross sections of variable thickness.

The final thickness of the support member 14 can be easily adjusted for a particular type of goggle design or application. For example, if a goggle to be worn over eyeglasses is desired, the thickness of support member 14 is made sufficient to provide clearance for eyeglasses. The final thickness will be dependent on the starting thickness and the degree of compression to which the foam is subjected. The amount of thickness reduction will also depend on the particular material used. After being heat pressed the support member 14 is generally planar and may be, for some materials, about one-tenth of its original thickness at the most compressed locations, resulting in a semi-rigid member. The support member 14 is preferably made of foam or cellular polyether urethane which can be extremely lightweight and easily contoured. For one polyether urethane foam that has been utilized, the initial density was about 1.7 pounds per cubic foot and the thickness before felting was about 2.8 inches. After felting, the thickness of the support member ranged from about 0.25 inches (a density of about 19 lbs/ft$^3$) at recessed areas 56 and 58 in FIG. 3 to about 1.0 inches (a density of about 4.8 lbs/ft$^3$) at thickness T$^3$ in FIG. 2. Alternatively, polyester urethane foam may be used for the support member 14 and still other plastic foams may be used to form the support member 14.

The shape of the support member 14 about its periphery conforms generally with the shape of the lens 12. The support member 14 has a centrally located, elongated opening 36 which defines the viewing area 26 of the lens 12 when the lens is secured to the support member. The support member 14 also has an upper portion 38, lower portion 40 and side portions 42 which are contiguous with and define the respective non-viewing areas 20, 22 and 24 of the lens 12.

The contours formed in the outer surface 32 of the support member 14 during the heat press operation include a plurality of spaced indentations forming upper air channels 44 and lower air channels 46. Each of the upper air channels 44 is positioned in the member 28 with respect to a lens aperture 18 such that a portion of the air channel, adjacent the upper edge or upper bead 48 of the member 14, is aligned with a respective lens aperture 18. The cooperation of upper bead 48 with apertures 18 air channels 44 define the openings for air channels 44. The length of the air channels 44, from the edge or bead 48 to the opening 36 is greater than the length of the aperture 18 so that air entering the apertures 18 does not flow directly into the face of the goggle wearer, but enters the aperture and is directed downward through the upper air channels 44 between the lens 12 and the support member 14 as shown in FIG. 2. The upper air channels 44 thus direct the air down across the inner surface 50 of the lens 12 and out through the lower air channels 46 through openings 52 formed between the lens 26 and the support member 14. Indentations 56 and 58 are also formed in opposite sides 42 of the outer surface 32 of the support member 14 to provide a recess between the lens and the support member to accommodate the goggle strap 13.

As an alternate embodiment, the goggle is similarly constructed but the lens has no apertures and the upper channels in the support member extend past the upper edge of the lens. The upper edge of the lens would, for example, extend straight across the top of the lens, such as along the bottom portions of apertures 18, indicated by reference numerals 18a in FIG. 3.

The upper edge or upper bead 48 of the support member 14 and a portion or lower bead 54 of the lower edge of the support member are raised to abut the respective upper and lower edges of the lens 12 and to extend slightly beyond the lens to guard the lens edges, preventing contact between the lens and the goggle wearer. Upper and lower bead 48 and 54 are not only aesthetically pleasing, but upper bead 48 also functions as an overhang to help keep snow, ice and water from contacting the goggle lens. Upper and lower beads 48 and 54 also facilitate alignment of lens member 26 on support member 14 during manufacture.

Figure 7:
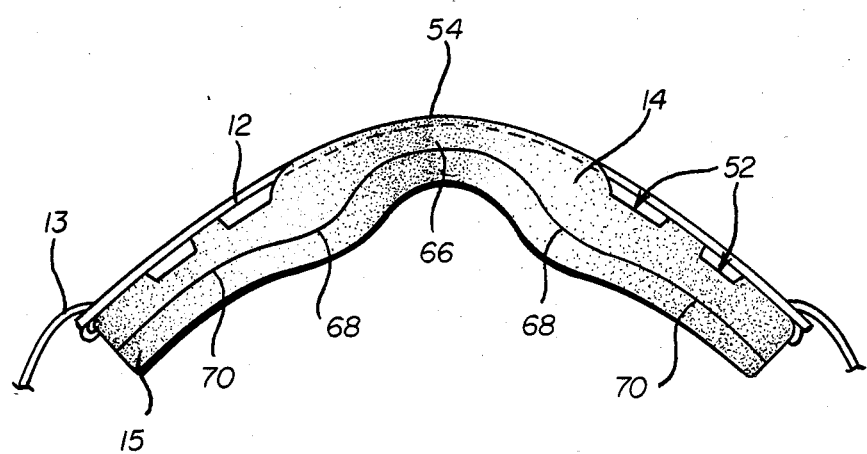
FIG. 7 view of the bottom of the goggle along line 7—7 of FIG. 1.

As can be seen from FIG. 2 and FIG. 7, the support member 14 has cross sections of variable thickness. Each of the air channels 44 and 46 formed in the support member 14 has a base 60 and side walls 62, wherein the side walls of each air channel have a cross section, the thickness ($T^2$) of which is greater than the thickness ($T^1$) of the cross section of the air channel base 60. Further, the thickness ($T^2$) of the side wall cross section is less than the thickness ($T^3$) of the cross section of the raised guard portions 48 and 54. It is the outer surface 32 of the side wall portions 62 of the support member 14 that the lens 12 rests on and is adhered to.

The inner surface 34 of the support member 14 is also preferably contoured during the heat press operation so that it will conform to general features of a face. More specifically, the inner surface 34 of the support member is inwardly contoured about the portion 66 of the member bridging a wearer's nose so that portion 66 is thinner than the portions 68 of the member positioned adjacent the base of the wearer's nose. From the portions 68, the surface 34 is again contoured inwardly about portions 70 to accommodate the cheeks of a goggle wearer.

The cushioning member 15 is stamped or cut out of a planar sheet of foam or cellular plastic. usually of uniform thickness, to provide a soft cushion which abuts the wearer's face when the goggle is worn. The member 15 may be made of the same type of foam as the support member 14. However the foam for the cushioning member 15 should be less dense than that forming the support member 14 to provide a cushion between the semirigid support member 14 and the face of the goggle wearer.

The goggle of the present invention is easily manufactured at a fraction of the cost of goggles having rubberized plastic frames, as will become apparent with reference to FIGS. 3–7. In order to manufacture the goggle 10 of the present invention, the individual planar components, the lens 12, support member 14 and cushioning member 15, are stamped out of planar sheets of transparent plastic and foam as discussed above, the contours of the support member 28 being formed by heat pressing or felting the foam after stamping the member 28 out.

Figure 4:
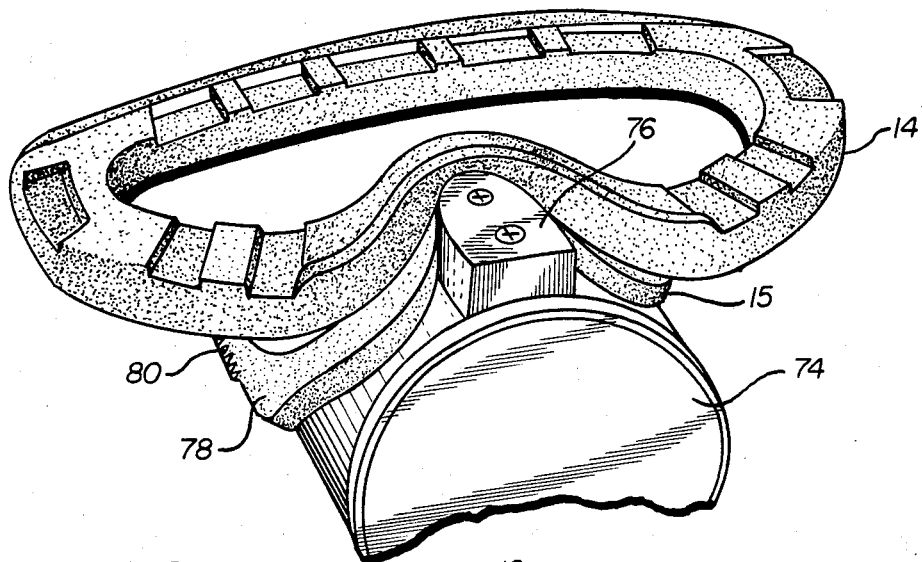
FIG. 4 is a perspective view of the support member as it is being secured to the cushioning member on a form, a fragmentary view of which is shown.
Figure 5:
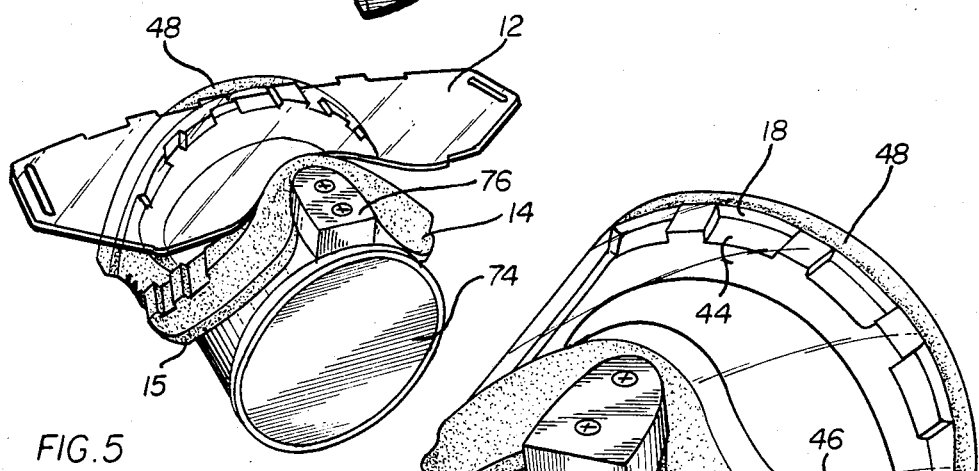
FIG. 5 is a perspective view of the lens as it is secured to the foam frame on the form.

In order to assemble the ski goggle 10, the cushioning member 15 is first secured about a generally circular form 74 having a radius which is slightly less than the desired radius of curvature of the finished ski goggle 10. The form 74 includes a block 76 attached thereto having a curved upper periphery to simulate the nose of a wearer and to maintain the goggle pieces 12, 14 and 15 in place on the form while the goggle is being made. As shown in FIG. 4, the cushioning member 15 is first positioned on the form 74 and held in place about the form by means of a strap 78 having on each end thereof a toothed clamp 80. An adhesive is applied to the outer surface of the cushioning member 15 to adhere the support member 14, positioned on top of the cushioning member, to the member 15. The support member 14 may be held in place on top of the cushioning member 15 by another strap having clamps on the ends thereof as shown in FIG. 5. Suitable adhesives are well known in the art for this purpose, such as contact cement, including, for example, urethane based adhesives.

Figure 6:
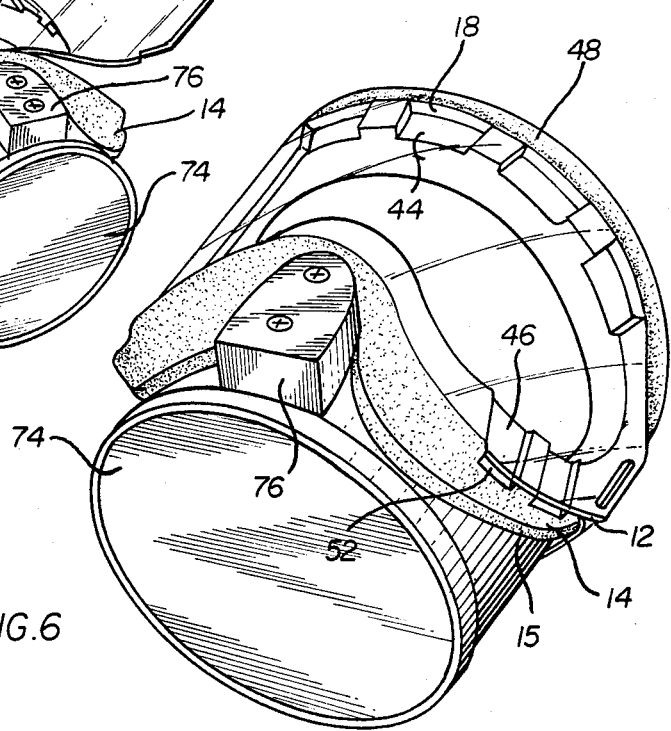
FIG. 6 is a perspective view of the goggle as it is formed on the form.

Next, while the support member is held curved about the form 74, an adhesive or bonding material is applied to the outer surface 32 of the side walls 62 of the support member 14 so that the lens may be adhered thereto. The lens 12 is positioned on the curved support member with the apertures 18 aligned with the air channels 44 and the upper edge of the lens abutting the guard 48. The lens 12 is deformed, as shown in FIG. 6, into a simple curve as it is adhered to the curved support member attached to the form 74. Once the adhesive securing the lens 12 to the support member 14 is set or cured to provide an adhesive bond, the curve of the lens is generally maintained even after the goggle is removed from the form 74 such that the radius of curvature of the lens 12 and goggle 10 is slightly greater than the radius of the form 74. Again, suitable adhesives are known in the art, such as hot melt adhesives and contact cement, including, for example, urethane based adhesives. Finally, the adjustable strap is inserted through the slots 16 and 17 of the lens.

In accordance with another embodiment, the adhesive material used to secure lens 12 to support member 14 and support member 14 to cushioning member 15 may be carried on both sides of a thin flexible substrate. For example, a carrier tape of material such as polyester film (Mylar ®) for example) can be coated with the suitable adhesive material for securing together the members of the goggle. A different adhesive could be used on each side of the carrier tape. For example, a pressure sensitive adhesive could be used on one side of the tape, such as the goggle side, with a heat activated adhesive (such as a urethane adhesive, for example) on the other side. The tape could also be of a desired color so that a visually pleasing aesthetic effect could be provided when viewing the goggle from the lens side. A removable backing, which could be paper, could be applied over the adhesive coated tape until it is ready for assembly with the goggle components.

When the support and lens members 14 and 12 are curved about form 74, the members have stored elastic energy. After the adhesive is cured and the goggle is released from the form, some of the stored elastic energy is released and the curvature of the goggle is reduced somewhat. Further release of elastic energy and straightening of the goggle components is prevented because further straightening would require relative movement of the support member 14 and the lens 12. The adhesive prevents such relative movement, and thus, the goggle maintains a self-supporting or self-sustaining curvature. Since the assembled goggle components have some flexibility, the goggle can be designed to fit the wearer's face, while maintaining a degree of flexibility for an exact fit without requiring an undue amount of bending or pressure on the wearer's face.

The anti-fog goggle of the present invention is extremely lightweight due to the foam support member 14 and thus more comfortable to wear. Further, because each member of the goggle, the lens 12, the support member 14 and the cushioning member 15 is normally planar and can be stamped out of planar sheets of plastic and foam and easily assembled from these planar members, manufacturing costs are relatively low. The anti-fog goggle of the present invention is thus less expensive although lighter in weight and more comfortable to wear than prior goggles.

While the goggle of the present invention has been described with respect to a cellular plastic frame member, it is to be understood that noncellular plastic or polymer materials may also be suitable for use in place of the cellular plastic frame member.

While the present invention has been described with respect to preferred embodiments, it will be understood that the invention is capable of numerous changes, modifications and additions and such changes, modifications and additions falling within the scope of the claims are intended to be covered thereby.

I claim:

1. A goggle comprising:
   a transparent, normally planar lens member deformed into a desired curvature, said lens member having a centrally located viewing area and non-viewing upper and lower peripheral areas;
   a normally planar semi-rigid support member for supporting said lens member and secured to said lens member and conforming to said desired curvature, said support member extending inwardly from the non-viewing areas of the lens member towards the face of the wearer of the goggle and having means disposed adjacent the upper and lower non-viewing areas of the lens member for forming, with portions of said upper and lower lens areas, respective upper and lower air channels to allow air to enter and exit the interior of the goggle between the lens and air channel forming means of the support member; and
   adhesive securing means for maintaining said lens member and said support member secured together in said desired curvature, the combination of said lens member and said support member secured together providing the goggle with curvature that is self-sustaining.

2. The goggle of claim 1 further comprising a layer of soft, resilient cushioning material to cushion contact with and conform to the face of the wearer, said cushioning material being mounted to the support member to extend inwardly thereof toward the wearer's face.

3. The goggle of claim 1 wherein said support member is made of cellular plastic and said air channel forming means includes indentations formed in the surface of the support to which the lens is secured.

4. The goggle of claim 1 wherein said support member is made of cellular polyether urethane.

5. The goggle of claim 1 wherein said support member is made of cellular polyester urethane.

6. The goggle of claim 2 wherein said support member is made of a plastic foam material and said cushioning material is made of a plastic foam material having a lower density than the density of said support member.

7. The goggle of claim 1 wherein said securing means comprises an adhesive bond.

8. The goggle of claim 7 wherein said normally planar lens and support members are bonded together with adhesive material while held in a curved position, whereby said lens and support members are maintained by said adhesive bond in said desired curvature.

9. The goggles of claim 7 wherein said adhesive bond together said support member and said lens member at peripheral portions of said lens member.

10. The goggle of claim 7 wherein said adhesive material is provided on both sides of a carrier tape located between said lens member and said support member.

11. The goggle of claim 10 wherein said carrier tape is polyester film.

12. The goggle of claim 3 wherein said securing means comprises an adhesive bond.

13. The goggle of claim 1 wherein said desired curvature is a substantially circular arc.

14. A goggle comprising:
   a normally planar transparent lens member deformed into a desired curvature, said lens member having inner and outer surfaces, a centrally located viewing area and peripheral non-viewing areas adjacent to the upper and lower edges of the viewing area, the upper non-viewing area having at least one lens aperture therein forming an air inlet,
   a normally planar semi-rigid support member having inner and outer surfaces and upper and lower areas, said support member for supporting said lens member and being secured to said lens and conforming to said desired curvature with the upper and lower areas of said support member being respectively at least substantially contiguous with the upper and lower non-viewing areas of said lens member, the outer surface of said support member having at least one lower air channel formed in said lower area and at least one upper air channel formed in said upper area, said upper air channel being aligned with said lens aperture to allow air to enter said upper air channel through the aperture, the air passing between the upper non-viewing area of the lens member and the upper area of the support member, across the viewing area of the lens member, and out through said lower air channel; and
   adhesive securing means for maintaining said lens member and said support member secured together in said desired curvature, the combination of said lens member and said support member secured together providing a goggle with curvature that is self-sustaining.

15. The goggle of claim 14 further comprising a layer of soft, resilient cushioning material to cushion contact with and conform to the face of the wearer, said cushioning material being mounted to the inner surface of said support member to extend inwardly thereof.

16. The anti-fog goggle of claim 14 wherein said support member includes upper and lower lens guard portions which respectively abut against portions of the upper and lower edges of said lens to guard said lens edges.

17. The anti-fog goggle of claim 16 wherein said support member has cross sections of variable thicknesses and each of said air channels has a base and two side walls, the side walls of each air channel having a cross section the thickness of which is greater than the thickness of the cross section of the air channel's base and less than the thickness of the cross section of the guard portions.

18. The goggle of claim 14 wherein said support member is formed of cellular plastic material.

19. The goggle of claim 14 wherein said support member is made of cellular polyether urethane.

20. The goggle of claim 14 wherein said support member is made of cellular polyester urethane.

21. The goggle of claim 14 wherein said securing means comprises an adhesive bond.

22. The goggle of claim 21 wherein said normally planar lens and support members are bonded together with adhesive material while held in a curved position, whereby said lens and support members are maintained by said adhesive in said desired curvature.

23. The goggle of claim 22 wherein said adhesive material is provided on both sides of a carrier tape located between said lens member and said support member.

24. The goggle of claim 23 wherein said carrier tape is polyester film.

25. The goggle of claim 21 wherein said adhesive bonds together said support member and said lens member at peripheral portions of said lens member.

26. The goggle of claim 14 wherein said desired curvature is a substantially circular arc.

27. A method of manufacturing a goggle comprising:
forming from a generally planar sheet of transparent plastic material an elongated generally planar semi-rigid lens member having a centrally located viewing area and upper and lower peripheral non-viewing areas;
forming from a generally planar sheet of foam material a generally planar semi-rigid support member having a centrally located elongated opening defining a viewing area;
deforming said lens and support members into a curved assembly position; and
adhesive securing said lens to one side of said support member while said lens and support members are in said curved assembly position whereby after said securing said lens and support members are in a desired curved assembled position.

28. The method of claim 27 wherein said step of forming said support member includes the step of forming air channels in the surface of said support member to which the lens is to be secured.

29. The method of claim 27 wherein said step of forming said lens includes the step of forming at least one aperture in said lens, said aperture to be aligned with one of said air channels in the support member when the lens is adhered to said member.

30. The method of claim 27 wherein said forming of said lens comprises stamping.

31. The method of claim 27 wherein said forming of said support member comprises stamping.

32. The method of claim 28 wherein said air channels are formed by heat pressing.

33. The method of claim 27 wherein said deforming comprises conforming the lens and support members about a form having the curve of said assembly position.

34. The method of claim 27 wherein said securing includes adhesively bonding with an adhesive said lens member to said support member.

35. The method of claim 34 wherein said lens and support members remain conformed to said form after said adhesively bonding until said adhesive is cured.

36. The method of claim 27 further comprising securing foam cushioning material to the side of said support member opposite the side having said lens member secured thereto.

37. The method of claim 27 further comprising forming a slot in each longitudinal end of said lens member.

38. The method of claim 37 further comprising disposing a headband in said slots.

39. A goggle comprising:
a normally planar transparent lens member deformed into a desired curvature, said lens member having inner and outer surfaces, a centrally located viewing area and peripheral non-viewing areas adjacent to the upper and lower edges of the viewing area, the upper non-viewing area having a plurality or lens apertures therein forming air inlets,
a normally planar semi-rigid cellular plastic support member having inner and outer surfaces and upper and lower areas, said support member for supporting said lens member and being secured to said lens and conforming to said desired curvature with the upper and lower areas of said support member being respectively at least substantially contiguous with the upper and lower non-viewing areas of said lens member, the outer surface of said support member having a plurality of lower air channels formed in said lower area and a plurality of upper air channels formed in said upper area, said upper air channels being aligned with said lens apertures to allow air to enter said upper air channels through the apertures, the air passing between the upper non-viewing area of the lens member and the upper area of the support member, across the viewing area of the lens member, and out through said lower air channels, said support member including upper and lower lens guard portions which respectively abat against portions of the upper and lower edges of said lens; and
an adhesive bond at peripheral portions of said lens member and said support member for maintaining said lens member and said support member secured together in said desired curvature, the combination of said lens member and said support member secured together with said adhesive bond providing a goggle with curvature that is self-sustaining.

40. The goggle of claim 39 further comprising a layer of soft, resilient cushioning material to cushion contact with and conform to the face of the wearer, said cushioning material being mounted to the inner surface of said support member to extend inwardly thereof.

* * * * *